United States Patent [19]

Wuchinich

[11] Patent Number: 4,526,571
[45] Date of Patent: Jul. 2, 1985

[54] CURVED ULTRASONIC SURGICAL ASPIRATOR

[75] Inventor: David G. Wuchinich, New York, N.Y.

[73] Assignee: Cooper LaserSonics, Inc., Santa Clara, Calif.

[21] Appl. No.: 434,567

[22] Filed: Oct. 15, 1982

[51] Int. Cl.³ .............................................. A61B 17/20
[52] U.S. Cl. .................................. 604/22; 128/24 A; 128/305
[58] Field of Search ................. 604/22, 46; 128/24 A, 128/303 R, 305, 303 C; 433/119; 360/323

[56] References Cited

U.S. PATENT DOCUMENTS

| | | | |
|---|---|---|---|
| 2,878,809 | 3/1959 | Treace | 128/303 R |
| 3,166,840 | 1/1965 | Bancroft et al. | 29/470 |
| 3,352,303 | 11/1967 | Delan | 604/22 |
| 3,433,226 | 3/1969 | Boyd | 128/305 |
| 3,693,613 | 9/1972 | Kelman | 128/24 A |
| 3,956,826 | 5/1976 | Perdreaux | 128/24 A |

Primary Examiner—C. Fred Rosenbaum
Assistant Examiner—J. L. Kruter
Attorney, Agent, or Firm—Vorys, Sater, Seymour and Pease

[57] ABSTRACT

An ultrasonic surgical aspirator having a transducer supported in a handpiece for generating ultrasonic vibrations which are transmitted to the tip of an operative probe through a transmitting structure including an elongated slender portion which is curved along at least a portion of its length to displace the longitudinal axis of the handpiece from the longitudinal axis of the probe attached to the end of the slender portion of the transmitting member to permit unobstructed vision along the probe. The radius of curvature of the curved portion of the transmitting structure is equal to or greater than 0.7 times the length of the longitudinal waves being transmitted.

12 Claims, 6 Drawing Figures

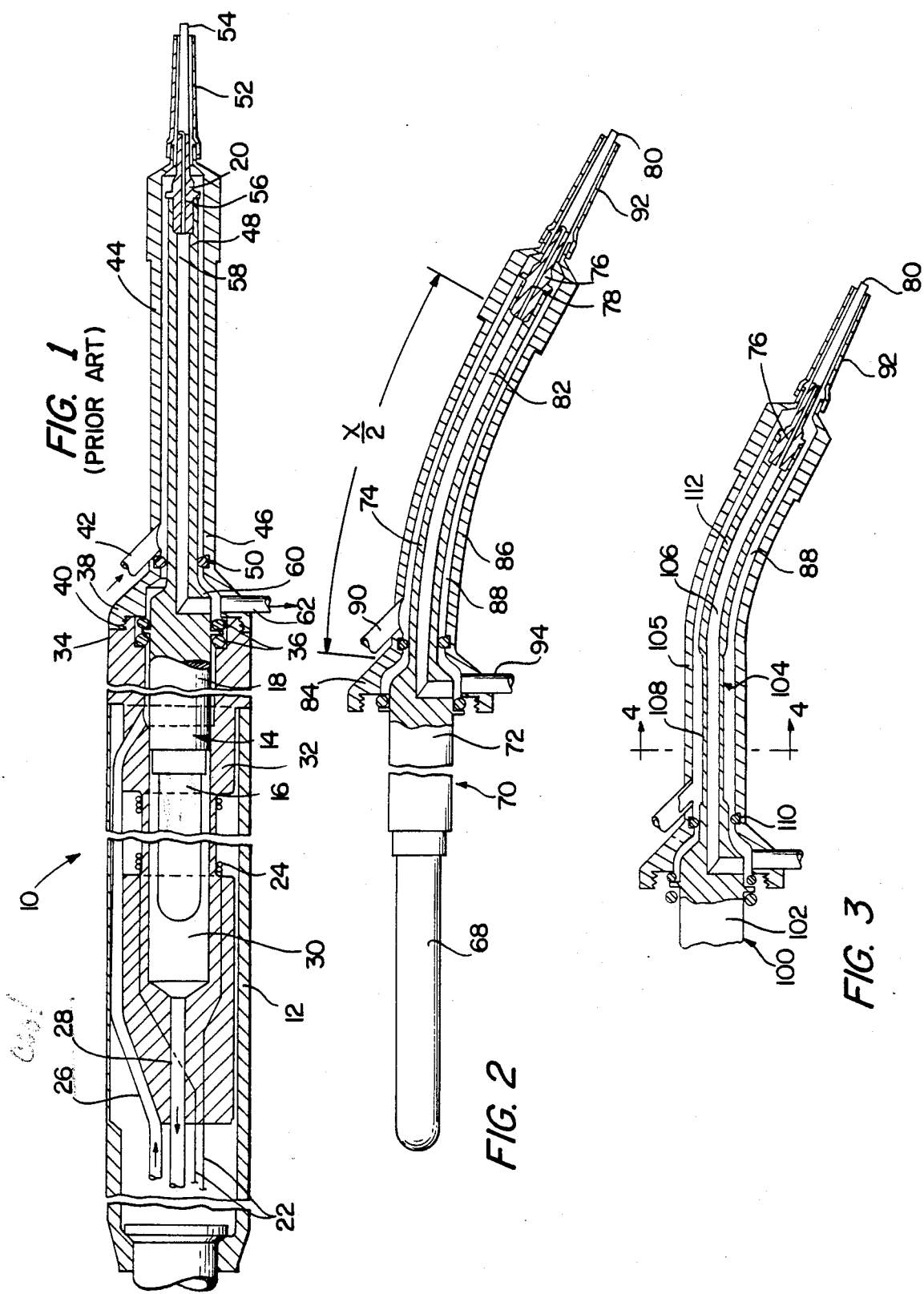

CURVED ULTRASONIC SURGICAL ASPIRATOR

BACKGROUND OF THE INVENTION

1. Field of the Invention

This invention relates to ultrasonic surgical instruments useful in removing tissue from within a biological structure, and more particularly to such an instrument having curved transmitting and/or amplifying structure to enable clear vision of the operating site with minimum loss of energy.

2. Description of the Prior Art

Surgical instruments utilizing ultrasonic vibrations in combination with the circulation of irrigation liquid over the operative site for the removal of tissue in a biological body are well known and widely used particularly in enclosed or substantially enclosed operative sites such as encountered in the removal of cataracts, brain tumors and other organ neoplasms. The known ultrasonic surgical aspirators of this type, generally referred to herein as ultrasonic aspirators, conventionally employ an elongated probe having one end rigidly attached through a vibration transmission member to a transducer for supplying ultrasonic energy, and having its other end portion adapted to be inserted into the operative site where the transmitted ultrasonic energy is emitted from the tip. Tissue particles are dislodged and broken up or emulsified by the ultrasonic energy and removed by the aspiration of irrigation fluid from the site.

The known ultrasonic handpieces generally employ piezoelectric elctromechanical transducers capable of transforming high frequency electrical energy into correspondingly high frequency mechanical impulses which are transmitted through the probe to the operative tip in a standing wave pattern. Such transducers require an enclosure or housing to provide the electrical connections required, to support the vibrating structure, to contain any circulating fluid necessary to cool the transducer, and to provide a surface that is not also vibrating for holding and manipulating the assembly. The housing, generally referred to as a handpiece, is dimensioned to fit comfortably into the surgeon's hand for easy manipulation and control during the surgical procedure.

One known ultrasonic surgical aspirator is disclosed in U.S. Pat. No. 3,805,787 and includes conduits for applying suction through the center of the vibration transmitting probe and for supplying irrigation fluid around the outer surface of the probe through a passage defined by a sleeve or shield. Irrigation fluid flows around the free end of the tubular probe element and back through the center of the probe to effectively irrigate and remove dislodged and emulsified tissue. Shield arrangements for controlling or directing the flow of irrigation fluid in the vicinity of the probe tip may be provided in accordance with this pior art patent, and U.S. Pat. No. 3,693,613 discloses a flow control system for avoiding the application of excessive pressure or suction at the operative site by such ultrasonic aspirator.

The known ultrasonic aspirators have employed straight ultrasonic transmission probes extending coaxially with the handpiece. Since the handpiece is substantially larger in diameter than the probe, and further since the handpiece is held in the surgeon's hand during use, view of the operative site at the tip of the probe is frequently obscured and consequently such devices are of limited use in removing tissue deep within a biological structure where the surrounding anatomy cannot be retracted or the opening made large enough to allow good visibility. Two examples of such situations are the extraction of brain tumors involving the optic nerve and removal of tumors within the colon. The application of the prior art straight ultrasonic aspirators is also particularly limited in microsurgery because the handpiece and the surgeon's hand often physically interfere with the surgical operating microscope, making simultaneous use of these instruments awkward if not impossible. Thus, however advantageous the application of intense ultrasonic vibration in the presence of irrigation and aspiration may be to surgery, the use of straight structures to provide this function limits the type and location of the malady amenable to approach.

Methods of and apparatus for transmitting longitudinal ultrasonic vibrations through both straight and curved structures, and for amplifying the intensity of the vibrations while undergoing such transmission are known. For example, U.S. Pat. No. 3,546,498 discloses a curved sonic transmission line in which the transmission element is made up of a series of straight and curved segments, the curves being relatively short radius bends located at critical locations, i.e., at the anodes in the vibrating transmission element. However, curved transmission elements have not been used in surgical ultrasonic aspirators despite the advantages to be obtained because, it is believed, that it has not been considered possible for longitudinal waves containing sufficient energy to be propagated through a curved transmission element independently of flexural waves of excessive magnitude and without such flexural waves interfering with the desired longitudinal movement of the operative tip of the probe.

SUMMARY OF THE INVENTION

In accordance with the present invention, an ultrasonic surgical aspirator is provided in which an ultrasonic transmission element is curved over a part of its length and supports a straight terminal end probe to permit the handpiece to be positioned out of the direct line of sight thereby enabling use of the device at an operative site deep in a biological structure. The curved section can be either an amplifying or a nonamplifying portion of the structure, but because curvature inherently introduces a component of motion perpendicular to the intended longitudinal vibrational direction, which component is proportional to the amplitude of the intended vibration at any point in the curved section, it may be preferred to introduce the curvature where the vibration is at a minimum. The component of motion perpendicular to the intended extensional vibration is parallel to the radius of curvature. In an ultrasonic aspiration device having a hollow or tubular probe, the curved section contains two effective radiating surfaces which are in contact with the aspiration and irrigation fluids passing through the device. To avoid excessive loss of transmitted power, the amplitude of the unintended component of motion may preferably be confined to the nonamplifying section of the structure. The curved section is preferably in the form of a relatively short arc of a circle having a radius which is equal to or greater than 0.7 times the wave length of the intended extensional vibration in the probe whereby substantially entensional or intended vibration only is transmitted from the curved section to the attached straight end portion of the transmitting structure.

BRIEF DESCRIPTION OF THE DRAWINGS

Other features and advantages of the invention will be apparent from the detailed description contained hereinbelow, taken in conjunction with the accompanying drawings, in which:

FIG. 1 is a longitudinal sectional view of a prior art ultrasonic surgical aspirator over which the present invention is an improvement;

FIG. 2 is a plan view, partially in section, of an ultrasonic aspirator embodying the present invention, with portions of the apparatus omitted;

FIG. 3 is a fragmentary plan view showing an alternate embodiment of the invention;

DESCRIPTION OF THE PREFERRED EMBODIMENTS

Figure 6:
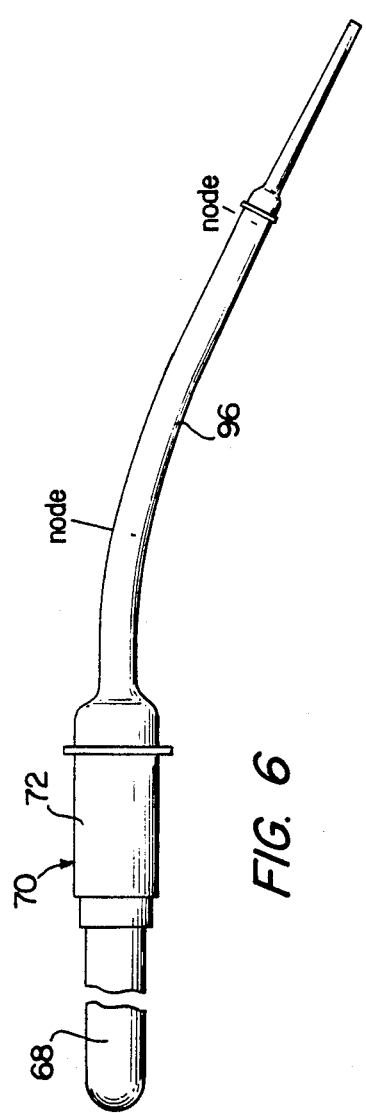
FIG. 6 is a fragmentary elevation view illustrating a modification of the invention shown in FIG. 2.
Figure 5:
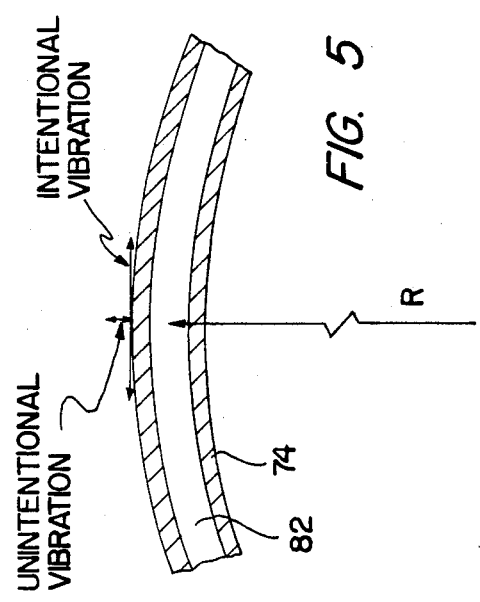
FIG. 5 is a fragmentary longitudinal sectional view of a portion of the curved section of the structure shown in FIG. 2.
Figure 4:
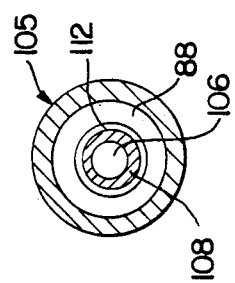
FIG. 4 is an enlarged sectional view taken on line 4—4 of FIG. 3.

Referring now to the drawings in detail, FIG. 1 shows an ultrasonic aspirator of the type illustrated, for example, in U.S. Pat. No. 3,693,613 and which is widely used in surgical practice. The ultrasonic aspirator is indicated generally by the reference numeral 10 and includes a handpiece or housing structure 12 enclosing and supporting a vibratory body 14 including a piezoelectric transducer element 16 and a transmitting element 18 terminating in outwardly spaced relation to the housing in an operative probe 20. Electric energy is provided from a suitable high frequency source, not shown, through conductors 22 to a coil 24 surrounding the transducer 16 within the handpiece 12. Inlet and outlet conduits 26, 28, respectively, supply a circulating cooling fluid within the handpiece for removing excess heat. The vibrating body assembly is mounted within a cavity 30 of a support element 32 which, in turn, is mounted on the end of and projects into the housing 12. A radially extending flange 34 disposed between a pair of resilient gasket members 36 effectively isolate the handpiece from vibrations induced by the transducer 16.

An irrigation and aspiration fluid housing 38 is mounted on the end of support element 32, as by a threaded connection 40, and retains the resilient gasket members 36 firmly in position. A fluid inlet 42 communicates with a cylindrical fluid chamber 44 between the hollow cylindrical body portion 46 of the housing 38 and the outer surface of the elongated tubular portion 48 of the transmitting body 18. An O-ring seal 50 is provided between members 46 and 48 to prevent the flow of irrigation fluid toward the handpiece. A removable sleeve member 52 is mounted on the distal end of housing 38 and extends in surrounding relation to the probe. Member 52 acts both as a shield for the vibrating probe and as a conduit for the irrigation fluid from chamber 44 to a position adjacent the operative tip 54 of the probe 20.

An aspiration passage 56 extends longitudinally through probe 20 from its operative tip 54 and communicates with an axial passage 58 in the elongated tubular portion 46 of the transmitting body. Passage 58 has an outlet into a chamber 60 within the housing 38 between O-ring seal 50 and gasket members 36, and an outlet conduit 62 communicating with the chamber 60 is connected to a source of vacuum, not shown, for aspirating the irrigation fluid and emulsified tissue from the operative site.

The construction and operation of the surgical ultrasonic aspirator according to the present invention may be substantially identical to the prior art apparatus just described except for the configuration of the vibration transmitting body and the irrigation and aspiration fluid housing structure. Thus, as seen in FIG. 2, in accordance with one embodiment of the invention, the vibrating structure includes a transducer 68 mounted on a transmitting body 70 adapted to be supported in the handpiece or housing in the manner described above. The transmitting body 70 includes a large diameter, solid cylindrical portion 72 adapted to be mounted in the cavity of the support member (not shown) of a handpiece, and an elongated tubular portion 74 of substantially smaller cross section. The tubular portion 74 has rigidly attached to its distal end an elongated straight probe member 76 having an axial bore 78 extending longitudinally therethrough from its free operative end 80. Bore 78 communicates with the central bore 82 in tubular portion 74 to provide a flow passage for aspiration fluid in the manner described above.

In the embodiment of FIG. 2, the tubular portion 74 of the transmitting body is of substantially uniform cross section from the inner, or supported end of probe 76 to the enlarged body portion 72, and its length between these points is preferably equal to one half the wave length of the longitudinal vibrations to be transmitted to the probe 76. Further, the enlarged body portion 72 is designed such that, for the particular material used to construct the transmitting body and the frequency of vibration used, the junction between portions 72 and 74 of the body occurs at a node in the longitudinal vibration pattern. This configuration therefore results in the effective cross-sectional change of the vibrating body resulting from the attachment of probe 76 to the tubular body portion 74 also being located at a node in the longitudinal vibration pattern. This configuration can, of course, be modified but is preferred for efficiency of vibration energy transmission.

Elongated tubular portion 74 of the transmitting body 70 is curved so that the longitudinal axis of the straight probe member 76 and the longitudinal axis of the transducer and the solid portion 72 of the transmitting body are disposed at an angle with respect to one another. The radius of curvature of section 74 is sufficiently large so that the velocity with which the vibrational waves introduced by the transducer travel through the curved structure is substantially equal to the velocity of the same vibrational waves through the structure if it were straight. This condition will exist in the ultrasonic surgical aspirator according to this invention if the radius of curvature, R, of the curved vibrating member is equal to or greater than 0.7 times the wave length ($\lambda$) of the vibration transmitted through the member. Thus, from a theoretical standpoint, the velocity of vibrational waves through an elongated slender curved member can be assumed to be the same as through a straight member of identical material and dimensions regardless of the degree of curvature provided that the radius of curvature is made sufficiently large. However, from a practical standpoint, it has been found that large degrees of curvature are not required for an ultrasonic surgical aspirator since the configuration of such instruments is such that displacement of the longitudinal axis of the straight probe from the axis of the handpiece of about 15° is usually sufficient to eliminate any obstruction of vision by the handpiece held in a surgeon's hand. Curvatures greater or less than 15° may be desired in some instances, however, in order to adapt an ultrasonic aspirator for a specific use.

As pointed out hereinabove, it is also generally known that purely extensional, or longitudinal, vibration can be recovered from an elongated slender ultrasonically vibrating member if a straight transmitting structure is attached to the curved portion at a point where there is little or no intentional motion, i.e., a motional node. Thus, when the length of the elongated tubular portion of the transmitting body is one half the wave length, or a multiple of this length, and where one node is located at the juncture of the large solid body portion and the elongated tubular structure, essentially pure longitudinal movement will be transmitted to the probe 76. This configuration is illustrated in FIG. 2 in which the elongated slender portion 74 of the transmitting body is uniformly curved throughout its length.

Still referring to FIG. 2 the aspiration fluid housing 84 employed in this embodiment is substantially identical to housing 38 described hereinabove, with the exception that the elongated cylindrical body 86 has a radius of curvature corresponding to the curvature of transmitting body portion 74 to provide a substantially uniform irrigation fluid channel 88 surrounding the outer surface of the transmitting body portion 74. Thus, irrigation fluid supplied through inlet 90 flows through channel 88 and over the outer surface of probe 76 within sleeve member 92 to be discharged adjacent the tip 80, then return through the drilled passage 86 and passage 82 to be removed through outlet tube 94.

Irrigation and aspiration liquid in chamber 88 and drill passage 82, respectively, will tend to absorb energy from unintentional vibrations in the curved section, i.e., vibrations parallel to the radius of curvature of the curved section. More energy may, therefore, be dissipated from a curved vibration element in an ultrasonic aspirator then would be dissipated from a correspondingly curved vibrating member surrounded by air or in a vacuum. Where energy loss may be critical, it may be desirable to introduce the curvature in the vibration transmitting element only in the vicinity of a vibrational node where there is no intentional vibrational movement or where such movement is minimal and consequently there will be minimal or no unintentional vibration. This is illustrated in FIG. 6 wherein a vibrational node in the elongated slender transmitting portion 96 is located within the relatively short curved portion of the element. From a practical standpoint, the necessary curvature cannot be introduced exactly at the node without producing a relatively sharp angle which would materially interfere with the vibrational characteristics. However, displacement and velocity increases from substantially zero at the nodes to a maximum at the antinodes located midway between adjacent nodes and therefore the curvature can extend from the nodes for some distance without introducing unacceptable transverse or unintentional vibrations and consequent energy loss. Again, however, in order to avoid unacceptable changes in vibrational characteristics, the radius of curvature should be sufficiently large to satisfy the condition of $R \geq 0.7\lambda$.

As indicated above, the ultrasonic aspirator according to the present invention may employ an amplifying or nonamplifying vibration transmission element, and an embodiment incorporating an amplifying transmission element is shown in FIG. 3. Since this embodiment is identical to that described above with regard to FIG. 2, except for the configuration of the elongated slender tubular portion of the transmitting member and the aspiration housing, only the portion of the structure necessary to illustrate this feature is shown. Thus, the vibration transmitting body 100 of this embodiment includes an enlarged solid portion 102 adapted to be received and supported in a handpiece of the type described above and an elongated slender transmitting portion 104 disposed centrally in aspiration housing 105. Portion 104 has an axial bore 106 extending therethrough for conveying aspiration fluid in a manner described above. The elongated slender transmitting body portion 104 includes a first section 108 of reduced cross-sectional area extending from a point adjacent the O-ring seal 110 along about one half its total length. The section of reduced cross section is preferably straight and may be of cylindrical cross section, although any desired cross-sectional configuration may be used. The reduced portion 104 is joined at its outer end to a larger section 112 which can be of a size and configuration corresponding to the elongated slender body portion 74 of the embodiment shown in FIG. 2. Section 112 is curved in the manner described with regard to FIG. 2 to orient the axis of the straight operative probe at the desired angle with respect to the longitudinal axis of the handpiece as previously described.

The section 104 acts as a vibrational amplifier in the known manner. In the configuration illustrated in FIG. 3, this amplifying section 104 is located closer to the transducer than the nonamplifying, curved section 112. It should be understood, however, that this arrangement could be reversed and it may in some instances be desirable to do so to avoid amplifications of the radially directed, or unintentional vibrations in the curved section. It should also be apparent that, although the amplifying section is illustrated as being straight in FIG. 3, this portion of the structure may also be curved or if desired the curvature may be limited to the amplifying portion of the structure.

As stated above, the velocity of vibrational waves traveling through a slender member of constant cross section should be substantially the same whether the slender member is straight or curved, so long as the radius of curvature satisfies the condition that $R \geq 0.7\lambda$. In practice, however, it has been found that in the construction of ultrasonic surgical aspirators, more favorable results are achieved where R is large enough to satisfy the relation $R \geq \lambda$. Of course, the greater the radius of curvature, the more precisely the velocity in the curved structure corresponds to the velocity in a straight structure; however, the length of the ultrasonic aspirator limits the length of the radius of curvature which can be employed and still provide the degree of curvature necessary to offset the handpiece from the line of sight along the straight operative probe. In practice it has been found that when the condition $R \geq 0.7$ is satisfied, the structure substantially duplicates the ultrasonic performance of the straight ultrasonic aspirator illustrated in FIG. 1.

While preferred embodiments of the invention have been disclosed and described, it should be understood that the invention is not so limited but rather that it is intended that all embodiments which would be apparent to one skilled in the art and which come within the spirit and scope of the invention are intended to be covered.

What is claimed is:

1. Ultrasonic surgical aspirator apparatus for breaking apart and removing tissue from a recessed operative site, comprising, transducer means operable to convert high frequency electrical energy to high frequency mechanical vibrations, elongated straight probe means having an axial bore extending therethrough, elongated vibration transmitting means having an enlarged body portion at one end operably connected with said transducer means and an elongated slender body portion at its other end operably associated with said probe means whereby longitudinal vibrations produced by said transducer means are transmitted to said probe, an elongated handpiece supporting said transmitting means and enclosing said transducer means, said elongated slender body portion of said transmitting means projecting outwardly from one end of said elongated handpiece and being curved along at least a portion of its length at a location spaced from said handpiece, the curvature of said slender body portion being the arc of a circle having a radius R of sufficient length to satisfy the condition $R \geq 0.7\lambda$, where $\lambda$ is the length of the longitudinal vibration wave transmitted and wherein the length of said elongated body portion is at least equal to one-half the wave length of the vibrations produced by said transducer means, said elongated slender body portion having an axial passage extending therethrough in communication with said axial bore in said probe for aspirating fluid and tissue therethrough from the operative site; and an irrigation fluid housing mounted on said handpiece and extending in parallel surrounding relation to and cooperating with said slender body portion to define an irrigation fluid passage for conducting irrigation fluid to be discharged adjacent the free end of said probe, and wherein said transducer is operable to generate a standing wave pattern in said transmitting means, said standing wave pattern including at least one node in said slender body portion adjacent said other end, said elongated probe being rigidly attached to said slender body portion substantially at a vibration node.

2. The ultrasonic surgical aspirator defined in claim 1 wherein said standing wave pattern includes two vibrational nodes one located adjacent each end of said elongated slender body portion.

3. The ultrasonic surgical aspirator defined in claim 2 wherein said elongated slender body portion is uniformly curved throughout its length between said two vibrational nodes.

4. The ultrasonic surgical aspirator defined in claim 1 wherein the included angle between the longitudinal axis of said straight probe means and the longitudinal axis of said transducer is at least about 15°.

5. The ultrasonic surgical aspirator defined in claim 1 wherein said elongated slender body portion is of substantially uniform cross section throughout its length.

6. The ultrasonic surgical aspirator defined in claim 1 wherein said elongated slender body portion is uniformly curved throughout substantially its full length.

7. The ultrasonic surgical aspirator defined in claim 1 wherein said elongated slender body portion includes a segment of reduced cross-sectional area extending along a portion only of its length, said segment of reduced cross-sectional area acting as a vibration amplifier.

8. The ultrasonic surgical aspirator defined in claim 1 further comprising an irrigation fluid housing mounted on said handpiece and extending in parallel surrounding relation to and cooperating with said slender body portion to define an irrigtion fluid passage for conducting irrigation fluid to be discharged adjacent the free end of said probe.

9. Ultrasonic surgical aspirator apparatus for breaking apart and removing tissue from a recessed operative site, comprising:

transducer means operable to convert high frequency electrical energy to high frequency mechanical vibrations;

elongated straight probe means having an axial bore extending therethrough, wherein the included angle between the longitudinal axis of said straight probe means and the longitudinal axis of said transducer means is at least approximately 15°;

elongated vibration transmitting means having an enlarged body portion at one end and operably connected with said transducer means, said transmitting means having an elongated slender body portion at its other end operably associated with said probe means such that longitudinal vibrations produced by said transducer means are transmitted to said probe, said elongated slender body portion including a segment of reduced cross sectional area extending along a portion only of its length, said segment of reduced cross sectional area acting as a vibration amplifier;

an elongated handpiece supporting said transmitting means and enclosing said transducer means;

said elongated slender body portion of said transmitting means projecting outwardly from one end of said elongated handpiece and being curved along at least a portion of its length at a location spaced from said handpiece, the curvature of said slender body portion being the arc of a circle having a radius R of sufficient length to satisfy the condition $R \geq 0.7\lambda$, where $\lambda$ is the length of the longitudinal vibration wave transmitted;

said elongated slender body portion having an axial passage extending therethrough in communication with said axial bore in said probe for aspirating fluid and tissue therethrough from the operative site; and an irrigation fluid housing mounted on said handpiece and extending in parallel surrounding relation to and cooperating with said elongated slender body portion to define an irrigation fluid passage for conducting irrigation fluid to be discharged adjacent the free end of said probe, and wherein said transducer means is adapted to generate a standing wave pattern in said transmitting means, said standing wave pattern including at least one node in said elongated slender body portion adjacent said other end, said elongated probe being rigidly attached to said elongated slender body portion substantially at a vibration node.

10. The ultrasonic surgical aspirator defined in claim 9 wherein said standing wave pattern includes two vibrational nodes one located adjacent each end of said elongated slender body portion.

11. The ultrasonic surgical aspirator defined in claim 9 wherein said segment of reduced cross-sectional area is substantially straight and wherein said elongated slender body portion is substantially uniformly curved throughout the portion thereof other than said segment of reduced cross-sectional area.

12. Ultrasonic surgical apparatus for breaking apart, irrigating, aspirating and removing tissue from a recessed surgical site, and adapted when in use to vibrate within a liquid medium, said apparatus comprising:

transducer means having a longitudinal axis and operable to convert high frequency electrical energy to high frequency mechanical vibrations;

elongated straight probe means operatively connected with said transducer means, said probe means having a longitudinal axis and having an axial bore extending therethrough for aspirating tissue and fluid from said surgical site, the longitudinal axis of said probe means and the longitudinal axis of said transducer means including an angle therebetween of at least approximately 15° for increasing visibility at said surgical site;

elongated vibration transmitting means having an enlarged body portion provided at a first end portion operatively associated with said transducer means and having an elongated slender body portion provided at a second end portion of said vibration transmitting means, said elongated slender body portion operatively connected with said probe means such that longitudinal vibrations produced by said transducer means are transmitted to said probe means in a standing wave pattern including at least one node in said slender body portion adjacent said second end portion of said vibration transmitting means, said probe means attached to said slender body portion substantially at a vibration node so as to minimize energy losses therebetween;

an elongated handpiece supporting said transmitting means and enclosing said transducer means, said elongated slender body portion of said transmitting means projecting outwardly from one end of said elongated handpiece and being curved along at least a portion of its length at a location spaced from said handpiece, the curvature of said slender body portion being the arc of a circle having a radius R of sufficient length to satisfy the condition $R \geq 0.7\lambda$, where $\lambda$ is the length of the longitudinal vibration wave transmitted through said elongated slender body portion, said elongated slender body portion having an axial passage extending therethrough in communication with said axial bore in said probe for aspirating fluid and tissue therethrough from said surgical site such that longitudinal waves containing sufficient energy are propagated through said elongated slender body portion independently of flexural waves of excessive magnitude and without such flexural waves interfering with desired longitudinal movement of said elongated straight probe means.

* * * * *